(12) United States Patent
Bushman et al.

(10) Patent No.: US 6,727,058 B2
(45) Date of Patent: Apr. 27, 2004

(54) INTERGRASE ASSAY

(75) Inventors: Frederic Bushman, Encinitas, CA (US); Mark Hansen, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 90 days.

(21) Appl. No.: 09/803,863

(22) Filed: Mar. 12, 2001

(65) Prior Publication Data

US 2001/0009772 A1 Jul. 26, 2001

Related U.S. Application Data

(63) Continuation of application No. 09/148,575, filed on Sep. 3, 1998, now Pat. No. 6,218,181, which is a continuation-in-part of application No. 09/044,085, filed on Mar. 18, 1998, now abandoned.

(51) Int. Cl.[7] .................................................. C12Q 1/70
(52) U.S. Cl. ............................... 435/5; 435/6; 435/69.1; 435/239; 435/183
(58) Field of Search ............................ 435/5, 6, 69.1, 435/239, 183

(56) References Cited

U.S. PATENT DOCUMENTS

| | | |
|---|---|---|
| 5,449,614 A | 9/1995 | Danos et al. |
| 5,470,726 A | 11/1995 | Miller et al. |
| 5,554,524 A | 9/1996 | Tevin et al. |
| 5,571,712 A | 11/1996 | Haynes et al. |
| 5,576,201 A | 11/1996 | Mason et al. |
| 5,591,624 A | 1/1997 | Barber et al. |
| 5,665,577 A | 9/1997 | Sodroski et al. |
| 5,686,279 A | 11/1997 | Finer |
| 5,747,307 A | 5/1998 | Lever |
| 5,750,396 A | 5/1998 | Yang et al. |
| 5,817,491 A | 10/1998 | Yee et al. |
| 6,013,516 A | 1/2000 | Verma et al. |

FOREIGN PATENT DOCUMENTS

| | | |
|---|---|---|
| WO | WO 91/05860 | 5/1991 |
| WO | WO 91/19798 | 12/1991 |
| WO | WO 93/17118 | 9/1993 |
| WO | WO 93/20220 | 10/1993 |

OTHER PUBLICATIONS

Wolfe et al., Journal of Virology 1996 vol. 70 (3), pp. 1424–1432.*
Farnet et al., PNAS 1996 Vol 93, pp. 9742–9747.*
Li et al., Journal of Virology 1998 Vol 72 (3), pp. 2125–2131.*
Anderson, W.F., "Human Gene Therapy," *Nature* 392:25–30 (1998).
Bennett, C.F., "Antisense Oligonucleotides: Is the Glass Half Full or Half Empty?," *Biochem. Pharmacol.* 55:9–19 (1998).
Blomer, et al., "Bcl–xL protects adult septal cholinergic neurons from axotomized cell death," *Proc. Natl. Acad. Sci. USA* 95:2603–2608 (1998).
Branch, A.D., "A good antisense molecule is hard to find," *TIBS* 23:45–50 (1998).
Buchschacher, et al., "Human Immunodeficiency Virus Vectors for Inducible Expression of Foreign Genes," *J. Virology* 66(5):2731–2739 (1992).
Bukrinsky, et al., "A nuclear localization signal within HIV–1 matrix protein that governs infection of non–dividing cells," *Nature* 365:666–669 (1993).
Burns, et al., "Vesicular stomatitis virus G glycoprotein pseudotyped retroviral vectors: Concentration to very high titer and efficient gene transfer into mammalian and non-mammalian cells," *Proc. Natl. Acad. Sci. USA* 90:8033–8037 (1993).
Carroll, et al., "A Human Immunodeficiency Virus Type 1 (HIV–1)–Based Retroviral Vector System Utilizing Stable HIV–1 Packaging Cell Lines," *J. Virology* 68(9):6047–6051 (1994).
Cohen, J., "New Role for HIV: A Vehicle For Moving Genes Into Cells," *Science* 272:195 (1996).
Crooke, S.T., "An Overview of Progress in Antisense Therapeutics" *Antisense & Nucl. Acid Drug Devel.* 8:115–122 (1998).
Dalgleish, et al., "Neutralization of Diverse HIV–1 Strains by Monoclonal Antibodies Raised against a gp41 Synthetic Peptide," *Virology* 165:209–215 (1988).
Deminie, et al., "Functional Exchange of an Oncoretrovirus and a Lentivirus Matrix Protein," *J. Virology* 68(7):4442–4449 (1994).
Ellison, et al. "Human Immunodeficiency virus integration in a cell–free system," *J. Virology* 64:2711–2715 (1990).
Fahraeus, et al., "New Approaches to Cancer Therapies," *J. Pathology* 187:138–146 (1999).
Farnet, et al. "Integration of human immunodeficiency virus type 1 DNA in vitro," *Proc. Natl. Acad. Sci. USA* 87:4164–4168 (1990).
Farnet, et al., "Differential inhibition of HIV–1 preintegration complexes and purified integrase protein by small molecules," *Proc. Natl. Acad. Sci. USA* 93:9742–9747 (1996).

(List continued on next page.)

Primary Examiner—Jeffrey Stucker
Assistant Examiner—Myron G Hill
(74) Attorney, Agent, or Firm—Knobbe, Martens, Olson & Bear, LLP (57) ABSTRACT

The present invention provides packaging cell lines and recombinant lentiviral or retroviral particles produced therefrom, particularly pseudotyped retroviral particles. The packaging cell lines of the invention are produced by inducibly expressing an envelope protein by methods described herein. Also described is a screening assay for compounds that affect integration of viral nucleic acid into target (e.g., host) nucleic acid. Such compounds are identified based on their effect on viral integrase.

13 Claims, 2 Drawing Sheets

OTHER PUBLICATIONS

Farnet, et al., "HIV–1 cDNA Integration: Requirement of HMG I(Y) Protein for Function of Preintegration Complexes In Vitro," *Cell* 88:483–492 (1997).

Farnet, et al., Human Immunodeficiency Virus Type 1 cDNA Integration: New Aromatic Hydroxylated Inhibitors and Studies of the Inhibition Mechanism, *Antimicrob. Agents and Chemo.* 42(9):2245–2253 (1998).

Gallay,et al., "HIV–1 Infection of Nondividing Cells: C–Terminal Tyrosine Phosphorylation of the Viral Matrix Protein Is a Key Regulator," *Cell* 80:379–388 (1995).

Goldman, et al., "Lentiviral Vectors for Gene Therapy of Cystic Fibrosis," *Human Gene Therapy* 8:2261–2268 (1997).

Gura, T., "Antisense Has Growing Pains," *Science* 270:575–577 (1995).

Hansen, et al., "Human Immunodeficiency Virus Type 2 Preintegration Complexes: Activities In Vitro and Response to Inhibitors," *J. Virology* 71(4):3351–3356 (1997).

Heinzinger, et al., "The V pr protein of human immunodeficiency virus type 1 influences nuclear localization of viral nucleic acids in nondividing host cells," *Proc. Natl. Acad. Sci. USA* 91:7311–7315 (1994).

Kay, et al., "Gene Therapy," *Proc. Natl. Sci. USA* 94:12744–12746 (1997).

Kim, et al., "A Short Sequence Upstream of the 5' Major Splice Site Is Important for Encapsidation of HIV–1 Genomic RNA," *Virology* 198:336–340 (1994).

Landau, et al., "Pseudotyping with Human T–Cell Leukemia Virus Type I Broadens the Human Immunodeficiency virus Host Range," *J. Virology* 65(1):162–169 (1991).

Ledley, F.D., "Clinical Considerations in the Design of Protocols for Somatic Gene Therapy," *Human Gene Therapy* 2:77–83 (1991).

Lewis, et al., "Human immunodeficiency virus infection of cells arrested in the cell cycle," *The EMBO J.* 11(8):3053–3058 (1992).

Lusso, et al., "Expanded HIV–1 Cellular Tropism by Phenotypic Mixing with Murine Endogenous Retroviruses," *Science* 247:848–852 (1990).

Mastrangelo,et al., "Gene Therapy for Human Cancer: An Essay for Clinicians," *Seminars in Oncology* 23(1):4–21 (1996).

Miller, et al., "Human Immunodeficiency Virus Type 1 Preintegration Complexes: Studies of Organization and Composition," *J. Virology* 71(7):5382–5390 (1997).

Naldini, et al., "In Vivo Gene Delivery and Stable Transduction of Nondividing Cells by a Lentiviral Vector," *Science* 272:263–267 (1996).

Naviaus, et al. "The pCL vector system: rapid production of helper–free, high–titer, recombinant retroviruses," *J. Virology* 5701–5705 (1996).

Page, et al., "Construction and Use of a Human Immunodeficiency Virus Vector for Analysis of Virus Infectivity," *J. Virology* 64(11):5270–5276.

Poznansky, et al., "Gene Transfer into Human Lymphocytes by a Defective Human Immunodeficiency Virus Type 1 Vector," *J. Virology* 65(1):532–536 (1991).

Richardson, et al., "Helper virus–free transfer of human immunodeficiency virus type 1 vectors," *J. Gen. Virology* 76:691–696 (1995).

Schwedler, et al., "The nuclear localization signal of the matrix protein of human immunodeficiency virus type 1 allows the establishment of infection in macrophages and quiescent T lymphocytes," *Proc. Natl. Acad. Sci. USA* 91:6992–6996 (1994).

Touchette, N., "Gene therapy: Not ready for prime time," *Nature Medicine* 2(1):7–8 (1996).

Trono, et al., "HIV–1 Gag Mutants Can Dominantly Interfere with the Replication of the Wild–Type Virus," *Cell* 59:113–120.

Verma, et al., "Gene therapy—promises, problems and prospects," *Nature* 389:239–242 (1997).

Yu, et al. "Inducible human immunodeficiency virus type 1 packaging cell lines," *J. Virology* 4530–4537 (1996).

ATCC Catalogue of Cell Lines & Hybridomas. 7edition, p. 148 (1992).

* cited by examiner

INTERGRASE ASSAY

RELATED APPLICATIONS

This application is a continuation of U.S. patent application Ser. No. 09/148,575, filed Sep. 3, 1998, now U.S. Pat. No. 6,218,181, which is a continuation-in-part of U.S. patent application Ser. No. 09/044,085, filed on Mar. 18, 1998, now abandoned.

GOVERNMENTAL INTEREST

This invention was made with Government support under Grant No. RO1 A134786 awarded by the National Institutes of Health. The Government has certain rights in this invention.

FIELD OF THE INVENTION

This invention relates generally to the field of recombinant retroviral particles for use in gene delivery and more specifically to packaging cell lines for producing retroviral particles.

BACKGROUND OF THE INVENTION

Retroviruses are enveloped RNA viruses that, after infection of a host cell, reverse transcribe their RNA genomes into a DNA intermediate, or provirus. All viruses containing an RNA genome and producing an RNA-dependent DNA polymerase are contained in the retroviral family. The family is divided into three subfamilies: (1) Oncovirinae, including all the oncogenic retroviruses, and several closely related non-oncogenic viruses; (2) Lentivirinae, the "slow retroviruses" such as the human immunodeficiency virus (HIV) and visna virus; and (3) Spumavirinae, the "foamy" retroviruses that induce persistent infections, generally without causing any clinical disease. Retroviruses containing at least three types of proteins encoded by the viral genome, i.e., gag proteins (the group antigen internal structural proteins), pol proteins (the RNA-dependent DNA polymerase and the protease and integrase proteins), and env proteins (the viral envelope protein or proteins). In addition to genes encoding the gag, pol, and env proteins, the genome to the retrovirus includes two long terminal repeat (LTR) sequences, one at the 5' and one at the 3' end of the virus. These 5' and 3' LTRs promote transcription and polyadenylation of viral mRNAs and participate in the integration of the viral genome into the cellular DNA of the host.

The provirus can be stably integrated into the host's cellular DNA. Gene products encoded by the provirus are then expressed by the host cell to produce retroviral virions, thereby replicating the virus. Because the retroviral genome can be manipulated to include exogenous nucleotide sequence(s) of interest for expression in a target cell, retroviral vectors are important tools for stable gene transfer into mammalian cells.

Many proposed gene therapy applications use retroviral vectors to take advantage of the ability of these naturally infectious agents to transfer and efficiently express recombinant nucleotide sequences in susceptible target cells. Retroviral vectors suitable for use in such applications are generally defective retroviral vector that are capable of infecting the target cell, reverse transcribing their RNA genomes, and integrating the reverse transcribed DNA into the target cell genome, but are incapable of replicating within the target cell to produce infectious retroviral particles (e.g., the retroviral genome transferred into the target cell is defective in gag, and/or in pol, see Coffin, J., In: RNA Tumor Viruses, Weiss, R. et al., (ed) Cold Spring Harbor Laboratory, Vol. 2, pp. 36–73, 1985).

Retroviral vectors and packaging cells (helper cells) have been developed to introduce recombinant nucleic acid molecules into mammalian cells without the danger of the production of replicating infectious virus. This methodology uses two components, a retroviral vector and a packaging cell. The retroviral vector contains long terminal repeats (LTRs), the foreign DNA to be transferred, and a packaging sequence. This retroviral vector will not reproduce by itself because the genes which encode the structural and envelope proteins are not included within the vector. The packaging cell contains genes encoding the gag, pol, and env proteins, but does not contain the packaging signal, so that the cell can only form empty virus particles by itself. With this method, the retroviral vector is introduced into the packaging cell, to create a cell able to produce virus. The cell manufactures viral particles containing only the retroviral vector DNA, and therefore has been considered safe.

Use of retroviral vectors is limited in many aspects. For example, although retroviruses can efficiently infect and stably integrate into the genome of rapidly-dividing cells, retroviral integration into the genome of non-dividing or slowly dividing cells is inefficient (Springett et al. 1989 *J. Virol.* 63:3865–3869; Miller et al. 1990 *Mol. Cell. Biol.* 10:4239–4242; Roe et al. 1993 *EMBO J.* 12:2099-2108). Most packaging systems provide only modest vector titers, and the fragility of retroviral vector particles complicate purification and concentration (Paul et al. 1993 *Hum. Gene Therap.* 4:609–615). Finally, retroviruses enter target cells by binding of retroviral envelope glycoproteins (encoded by the env gene) to specific target cell surface receptors. This envelope protein-cell surface receptor interaction is often species specific, and in some cases even tissue specific. Moreover, the level of expression of the cell surface receptor on the target cells can vary widely among target cells. As a result, retroviruses usually have a limited host range (Kavanaugh et al. 1994 *Proc. Natl. Acad. Sci. USA* 91:7071–7075; Hopkins 1993 *Proc. Natl. Acad. Sci. USA* 90:8759–8760).

One strategy for both expanding retroviral host cell range and structural stability of the retroviral virion involves production viral vectors. Pseudotyped retroviral vectors useful in transformation of target cells are generally composed of retroviral virion structural proteins (e.g., gag proteins), a recombinant RNA genome containing the nucleotide sequence of interest, the pol protein for reverse transcription of the recombinant RNA contained in the virion, and a non-retroviral envelope protein or an envelope protein from a different retrovirus. The recombinant RNA genome is usually replication defective, e.g., defective in the pol and/or gag genes, to prevent production of infectious retrovirus following transfer of the nucleotide sequence of interest into the target cell. The envelope protein of the pseudotyped retroviruses normally selected to provide a broader host range or to provide selective targeting of cells to be infected.

SUMMARY OF THE INVENTION

The present invention provides packaging cell lines and recombinant retroviral particles produced therefrom, particularly pseudotyped retroviral particles. Exemplary packaging cell lines are derived from 293 HeLa, Cf2Th, D17, MDCK, or BHK cells, most preferably from 293 cells. Retroviral particles are produced by inducibly expressing an envelope protein of interest (e.g., a retroviral envelope or the envelope protein of vesicular stomatitis virus (VSV G)).

Inducible expression of the envelope protein is accomplished by operably linking an envelope protein-encoding nucleotide sequence to an inducible promoter (e.g., a promoter composed of a minimal promoter linked to at least one copy of tetO, the binding site for the tetracycline repressor (tetR) of the *Escherichia coli* tetracycline resistance operon Tn10). Expression from the inducible promoter is regulated by a transactivating factor, composed of a first ligand-binding domain that negatively regulates transcription from the inducible promoter (e.g., a prokaryotic tetracycline repressor polypeptide (tet R)). Transcription of the envelope-encoding nucleotide sequence under control of the inducible promoter is activated by a transactivator when tetracycline is absent.

A primary object of the invention is to provide a packaging cell line that produces retroviral particles, especially pseudotyped retroviral particles, more efficiently (e.g., at higher titers) than conventional packaging cell lines. The packaging cell line of the invention is characterized by a first polynucleotide having an HIV genome operably linked to a first inducible promoter wherein the HIV genome is defective for cis-acting elements, for self-replication and for expression of functional Env protein; a second polynucleotide encoding a functional heterologous Env protein operably linked to a second inducible promoter; and a third polynucleotide encoding a regulatable transcriptional activator controlling transcription from the first and second inducible promoters.

Another object of the invention is to provide recombinant retroviral vectors, especially pseudotyped retroviral vectors, that are useful in both in vitro and in vivo transformation of a target cell.

An advantage of the invention is that packaging cell lines can be produced that contain an envelope-encoding nucleotide sequence stably integrated in the cell's genome, which sequence can be inducibly expressed, thus allowing generation of packaging cell lines capable of expressing an envelope protein that is otherwise toxic to the host cell (e.g., VSV G). Another advantage of the invention is that the packaging cell lines do not have the potential to produce replication competent retroviruses.

In another embodiment, the invention provides a method for producing a packaging cell line. The method includes transfecting a suitable cell with i) a first polynucleotide having an HIV genome operably linked to a first inducible promoter wherein the HIV genome is defective for cis-acting elements, for self-replication and for expression of functional Env protein; ii) a second polynucleotide encoding a functional heterologous Env protein operably linked to a second inducible promoter; and iii) a third polynucleotide encoding a regulatable transcriptional activator controlling transcription from the first and second inducible promoters; and culturing the transfected cells above under conditions which allow screening for cells containing proteins encoded by the polynucleotides. Preferably, the cell is co-transfected with a selectable marker encoding polynucleotide, such as an antibiotic resistance gene.

In another embodiment, the invention provides a method of detecting a viral nucleic acid sequence integrated into a target nucleic acid sequence by reversibly immobilizing the target nucleic acid sequence to a solid support, contacting the target nucleic acid with a viral preintegration complex (PIC) containing the viral nucleic acid sequence, under such conditions and for sufficient time so as to allow the viral nucleic acid sequence to integrate into the target nucleic acid sequence and detecting the integrated viral nucleic acid sequence.

In yet another embodiment, the invention provides a method of detecting viral integrase activity contained in viral preintegration complex (PIC). The method includes reversibly immobilizing a target nucleic acid sequence to a solid support; contacting the target nucleic acid with the viral preintegration complex (PIC) containing a viral nucleic acid sequence, under such conditions and for sufficient time so as to allow the viral nucleic acid sequence to integrate into the target nucleic acid sequence and detecting the integrated viral nucleic acid sequence. The presence of the viral nucleic acid sequence in the target nucleic acid sequence is indicative of integrase activity.

In a further embodiment, the invention provides a method of identifying a compound that affects viral integrase activity contained in a preintegration complex (PIC). The method includes reversibly immobilizing a target nucleic acid sequence to a solid support; contacting the target nucleic acid with the viral preintegration complex (PIC) containing a viral nucleic acid sequence and a test compound suspected of affecting integrase activity, under such conditions and for sufficient time so as to allow the viral nucleic acid sequence to integrate into the target nucleic acid sequence; and detecting the integrated viral nucleic acid sequence. The amount of viral nucleic acid sequence integrated in the target nucleic acid sequence is indicative of the effect of the compound on integrase activity.

These and other objects, advantages and features of the present invention will become apparent to those persons skilled in the art upon reading the details of the vectors, cell lines and methodology as more fully set forth below.

DESCRIPTION OF THE PREFERRED EMBODIMENTS

Before the present inducible expression system, use of the inducible expression system to generate packaging cell lines for retroviral vectors pseudotyped with VSV G, and constructs, vector particles, and packaging cell lines associated therewith are described, it is to be understood that this invention is not limited to the particular methodology, protocols, cell lines, retroviruses, vectors, constructs, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a packaging cell" includes a plurality of such cells and reference to "the retroviral vector" includes reference to one or more vectors and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, and methodologies which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Definitions

By "inducible expression system" is meant a construct or combination of constructs that includes a nucleotide sequence encoding a transactivator, an inducible promoter that can be transcriptionally activated by the transactivator, and a nucleotide sequence of interest operably linked to the inducible promoter. For example, an exemplary inducible expression system of the invention includes a nucleotide sequence encoding a tetracycline operon regulatable transactivator (tTA) and a nucleotide sequence of interest operably linked to an inducible promoter composed of a minimal promoter operably linked to at least one tetO sequence.

By "transactivator," "transactivating factor," or "transcriptional activator" is meant a polypeptide that facilitates transcription from a promoter. Where the promoter is an inducible promoter, the transactivator activates transcription in response to a specific transcriptional signal or set of transcriptional signals. For example, in the inducible expression system of the invention, tTA is a transactivator that facilitates transcription from the inducible tetO promoter when tTA is not bound to tetracycline.

"Tetracycline repressor protein," tetracycline repressor polypeptide," "tetR polypeptide," and "tetR protein" are used interchangeably herein to mean a polypeptide that exhibits both 1) specific binding to tetracycline and/or tetracycline derivatives; and 2) specific binding to tetO sequences when the tetR polypeptide is not bound by tetracycline or a tetracycline analog(s). "TetR polypeptide" is meant to include a naturally-occurring (i.e., native) tetR polypeptide sequence and functional derivatives thereof.

By "transcriptional activation domain" is meant a polypeptide sequence that facilitates transcriptional activation from a promoter. "Transcriptional activation domain" includes transcriptional activation domains derived from the naturally-occurring amino acid sequence of a transcription factor as well as functional derivatives thereof.

By "envelope protein" is meant a polypeptide that 1) can be incorporated into an envelope of a retrovirus; and 2) can bind target cells and facilitate infection of the target cell by the RNA virus that it envelops. "Envelope protein" is meant to include naturally-occurring (i.e., native) envelope proteins and functional derivatives thereof that 1) can form pseudotyped retroviral virions according to the invention, and 2) exhibit a desired functional characteristic(s) (e.g, facilitate viral infection of a desired target cell, and/or exhibit a different or additional biological activity). In general, envelope proteins of interest in the invention include any viral envelope protein that can, in combination with a retroviral genome, retroviral Pol, retroviral Gag, and other essential retroviral components, form a retroviral particle. Such envelope proteins include retroviral envelope proteins derived from any suitable retrovirus (e.g., an amphotropic, xenotropic, ecotropic or polytropic retrovirus) as well as non-retroviral envelope proteins that can form pseudotyped retroviral virions (e.g., VSV G). Envelope proteins of particular interest include, but are not limited to, envelope protein of vesicular stomatis virus (VSV G), HTLV-1, gibbon ape leukemia virus (GALV), Sindai virus, influenza virus, herpes virus, rhabdovirus, and rabies virus.

By "functional derivative of a polypeptide" is meant an amino acid sequence derived from a naturally-occurring polypeptide that is altered relative to the naturally-occurring polypeptide by virtue of addition, deletion, substitution, or other modification of the amino acid sequence. "Functional derivatives" contemplated herein exhibit the characteristics of the naturally-occurring polypeptide essential to the operation of the invention. For example, by "functional derivative of tetR" is meant a polypeptide derived from tetR that retains both 1) tetracycline or tetracycline analog binding and 2) the ability to inhibit transcriptional activation by tTA when bound to tetracycline or an analog thereof.

By "promoter" is meant a minimal DNA sequence sufficient to direct transcription of a DNA sequence to which it is operably linked. The term "promoter" is also meant to encompass those promoter elements sufficient for promoter-dependent gene expression controllable for cell-type specific expression, tissue-specific expression, or inducible by external signals or agents; such elements may be located in the 5' or 3' regions of the naturally-occurring gene.

By "inducible promoter" is meant a promoter that is transcriptionally active when bound to a transcriptional activator, which in turn is activated under a specific condition(s), e.g., in the presence of a particular chemical signal or combination of chemical signals that affect binding of the transcriptional activator to the inducible promoter and/or affect function of the transcriptional activator itself. For example, the transcriptional activator of the present invention, tTA, induces transcription from its corresponding inducible promoter when tetracycline is absent, i.e. tetracycline is not bound to tTA.

By "construct" is meant a recombinant nucleotide sequence, generally a recombinant DNA molecule, that has been generated for the purpose of the expression of a specific nucleotide sequence(s), or is to be used in the construction of other recombinant nucleotide sequences. In general, "construct" is used herein to refer to a recombinant DNA molecule.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that a nucleotide sequence of interest is positioned adjacent a nucleotide sequence that directs transcription and translation of the introduced nucleotide sequence of interest (i.e., facilitates the production of, e.g., a polypeptide encoded by a DNA of interest).

By "packaging cell line" is meant a line of packaging cells selected for their ability to package defective retroviral vectors at a titer of generally greater than $10^3$ virions per milliliter of tissue culture medium, having less than 10 helper virus virions per milliliter of tissue culture medium, and capable of being passaged in tissue culture without losing their ability to package defective retroviral vectors.

By "transformation" is meant a permanent or transient genetic change, preferably a permanent genetic change, induced in a cell following incorporation of new DNA (i.e., DNA exogenous to the cell). Where the cell is a mammalian cell, a permanent genetic change is generally achieved by introduction of the DNA into the genome of the cell.

By "target cell" is meant a cell(s) that is to be transformed using the methods and compositions of the invention. Transformation may be designed to non-selectively or selectively transform the target cell(s). In general, target cell as used herein means a eukaryotic cell that can be infected by a VSV G pseudotyped retroviral vector according to the invention.

By "transformed cell" is meant a cell into which (or into an ancestor of which) has been introduced, by means of recombinant DNA techniques, a DNA molecule encoding a gene product (e.g., RNA and/or protein) of interest (e.g., nucleic acid encoding a therapeutic cellular product).

By "nucleotide sequence of interest" or "DNA of interest" is meant any nucleotide or DNA sequence that encodes a protein or other molecule that is desirable for expression in a host cell (e.g., for production of the protein or other biological molecule (e.g., a therapeutic cellular product) in the target cell). The nucleotide sequence of interest is generally operatively linked to other sequences which are needed for its expression, e.g., a promoter. In general, a nucleotide sequence of interest present in the genome of a recombinant retroviral particle of the invention encodes any gene product of interest, usually a therapeutic gene product where the recombinant retroviral particle is to be used to transform cells in vivo (e.g., in a gene therapy application in humans).

By "therapeutic gene product" is meant a polypeptide, RNA molecule or other gene product that, when expressed in a target cell, provides a desired therapeutic effect, e.g., repair of a genetic defect in the target cell genome (e.g., by complementation), expression of a polypeptide having a desired biological activity, and/or expression of an RNA molecule for antisense therapy (e.g., regulation of expression of a endogenous or heterologous gene in the target cell genome).

By "subject" or "patient" is meant any subject for which cell transformation or gene therapy is desired, including humans, cattle, dogs, cats, guinea pigs, rabbits, mice, insects, horses, chickens, and any other genus or species having cells that can be infected with a viral vector having an envelope containing VSV G or other envelope described herein.

By "transgenic organism" is meant a non-human organism (e.g., single-cell organisms (e.g., yeast), mammal, non-mammal (e.g., nematode or Drosophila)) having a non-endogenous (i.e., heterologous) nucleic acid sequence present as an extrachromosomal element in a portion of its cells or stably integrated into its germ line DNA.

By "transgenic animal" is meant a non-human animal, usually a mammal, having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

By "viral vector" is meant a recombinant viral particle that accomplishes transformation of a target cell with a nucleotide sequence of interest.

By "virion," "viral particle," or "retroviral particle" is meant a single virus minimally composed of an RNA genome, Pol protein (for reverse transcription of the RNA genome following infection), Gag protein (structural protein present in the nucleocapsid), and an envelope protein. As used herein, the RNA genome of the retroviral particle is usually a recombinant RNA genome, e.g., contains an RNA sequence exogenous to the native retroviral genome and/or is defective in an endogenous retroviral sequence (e.g., is defective in pol, gag, and/or env, and, as used herein, is normally defective in all three genes).

By "pseudotyped viral particle," or "pseudotyped retroviral particle" is meant a viral particle having an envelope protein that is from a virus other than the virus from which the RNA genome is derived. The envelope protein can be from a retrovirus of a species different from the retrovirus from which the RNA genome is derived or from a non-retroviral virus (e.g., vesicular stomatitis virus (VSV)). Preferably, the envelope protein of the pseudotyped retroviral particle is VSV G.

By "VSV G" or "VSV G envelope protein" is meant the envelope protein of vesicular stomatitis virus (VSV) or a polypeptide derived therefrom or recombinant fusion polypeptide having a VSV G polypeptide sequence fused to a heterologous polypeptide sequence, where the VSV G-derived polypeptide of recombinant fusion polypeptide can be contained in a viral envelope of a pseudotyped retroviral particle and retains infectivity for a desired target cell (e.g., a range of desired eukaryotic cells, or a specific target cell of interest).

By "VSV G pseudotyped virus," "VSV G pseudotyped retrovirus," "VSV G pseudotyped viral particle," or "VSV G pseudotyped retroviral particle," is meant a retrovirus having the envelope protein VSV G, e.g., either in combination with or substantially substituted for the endogenous retroviral envelope. Preferably, VSV G is present in the VSV G pseudotyped viral envelope such that VSV G represents about 50% of the envelope protein(s) present in the envelope, more preferably about 75%, even more preferably about 90% to about 95%, still more preferably greater than about 95%, most preferably about 100% or such that VSV G is substantially the only envelope protein present in the pseudotyped viral particle envelope.

The invention will now be described in further detail.

Packaging Cell Line and Transactivator

In a first embodiment, the invention provides a packaging cell line which includes a first polynucleotide having an HIV genome operably linked to a first inducible promoter wherein the HIV genome is defective for cis-acting elements, for self-replication and for expression of functional Env protein; a second polynucleotide encoding a functional heterologous Env protein operably linked to a second inducible promoter; and a third polynucleotide encoding a regulatable transcriptional activator controlling transcription from the first and second inducible promoters.

The first polynucleotide includes an HIV genome that is incapable of self-replication and encodes gag and pol but not env, and does not contain a packaging signal or long-terminal repeats (LTRs). The second polynucleotide encodes a heterologous Env or "envelope protein" as described above in the definitions.

The third polynucleotide encodes a regulatable transcriptional activator, or transactivator, which controls transcription from the first and second inducible promoters, which regulate expression of the first and second polynucleotides described above.

In a preferred embodiment, the first, second and third polynucleotides are contained in vectors. These polynucleotides can be contained in one or more vectors, preferably plasmid vectors. In the exemplary packaging cell line of the invention, the first polynucleotide is contained in a first plasmid vector referred to pPTK and the second polynucleotide is contained in second plasmid vector referred to as pBIGFVG. The second vector contains the VSV envelope as well as green fluorescent protein as an indicator marker. The third polynucleotide encoding a regulatable transcriptional activator is exemplified herein as containing a minimal CMV immediate-early gene promoter linked to seven tandem copies of the tetr-binding site replaced the CMV promoter(BgIII/BamHI fragment), in pcDNAneo to create phCMVn. As discussed herein, other viral envelopes and other indicator markers will be known to those of skill in the art for use in the present invention.

In one aspect of the invention, one or more polynucleotides encoding retroviral accessory proteins, are included as part of the first or second polynucleotide constructs, for example. Accessory proteins include vpr, vif, nef, vpx, tat, rev, and vpu Preferably, the transcriptional activator, or transactivator can be expressed at high levels in a eukaryotic cell without significantly adversely affecting general cellular transcription in the host cell transactivator expression that is sufficient to facilitate transactivation of the inducible promoter, but that is not detrimental to the cell (e.g., is not toxic to the cell). "High levels" can be a level of expression that allows detection of the transactivator by Western blot. The transactivator can preferably be expressed in a wide variety of cell types, including mammalian and non-mammalian cells such as, but not limited to, human, monkey, mouse, hamster, cow, insect, fish, and frog cells.

The transactivator can be expressed either in vivo or in vitro, and expression of the transactivator can be controlled through selection of the promoter to which the nucleotide sequence encoding the transactivator is operably linked. For example, the promoter can be a constitutive promoter or an inducible promoter. Examples of such promoters include the human cytomegalovirus promoter IE (Boshart et al., 1985 Cell 41:521–530), ubiquitously expressing promoters such as HSV-Tk (McKnight et al., 1984 Cell 37:253–262) and β-actin promoters (e.g. the human β-actin promoter as described by Ng et al., Mol. Cell Biol. 1985 5:2720–2732).

The promoter of the transactivator can be a cell type-specific or tissue-specific promoter that preferentially facilitates transcription of the transactivator in a desired cell of tissue type. Exemplary cell type-specific and/or tissue-specific promoters include promoters such as albumin (liver specific; Pinkert et al., 1987 Genes Dev. 1:268–277), lymphoid specific promoters (Calame et al., 1988 Adv. Immunol. 43:235–275); in particular promoters of T-cell receptors (Winoto et al., 1989 EMBO J. 8:729–733) and immunoglobulins; Banerji et al., 1983 Cell 33729–740; Queen and Baltimore, ibid. 741–748), neuron-specific promoters (e.g. the neurofilament promoter; Byrne et al., 1989 Proc. Natl. Acad. Sci. USA 86:5473–5477), pancreas-specific promoters (Edlunch et al., 1985 Science 230:912–916) or mammary gland-specific promoters (milk whey promoter, U.S. Pat. No. 4,873,316 and European Application Publication No. 264,166). Promoters for expression of the transactivator can also be developmentally-regulated promoters such as the murine homeobox promoters (Kessel et al., 1990 Science 249:374–379) or the α-fetoprotein promoter (Campes et al., 1989 Genes Dev. 3:537–546). The promoter can be used in combination with control regions allowing integration site independent expression of the transactivator (Grosveld et al., 1987 Cell 51:975–985). Preferably, the promoter is constitutive in the respective cell types. Preferably the promoter is a CMV promoter, more preferably a CMV immediate early gene promoter.

Preferably, the transactivator is a native tetR polypeptide or a functional derivative of tetR, since tetR binds its specific DNA sequence (tetO) with greater affinity than either lacR or GAL4 bind their respective sequences. For example, tetR binds tetracycline much tighter ($k_a \approx 10^9$ M$^{-1}$; Takahashi et al., J. Mol. Biol. 187:341–348 (1986) than lacR complexes IPTG ($k_a \approx 10^6$ M$^{-1}$; Barkley & Bourgeios in The Operon, Miller & Rezinkoff, eds., Cold Spring Harbor Lab., Cold Spring Harbor, N.Y., 1980, pp. 177–220). Thus, very low, nontoxic concentrations of tetracycline function effectively. By "functional derivative of tetR" is meant a polypeptide derived from tetR that retains both 1) tetracycline or tetracycline analog binding and 2) the ability to inhibit transcription from the inducible promoter by preventing binding of the tetR domain to tetO sequences within the inducible promoter. The nucleotide sequence encoding tetR can be obtained according to Postel et al., 1984 Nucl. Acids Res. 2:4849–4863, herein incorporated by reference. Other tetR sequences useful in the invention, and the respective binding sites for these repressors, are described in (Waters et al., 1983 Nucl. Acids Res. 11:6089–6105; Postle et al., supra; Unger et al., 1984 Gene 31:103–108; Unger et al., 1984 Nucl. Acids Res. 127693–7703; Tovar et al., 1988 Mol. Gen. Genet. 215:76–80); for comparison and overview see Hillen and Wissmann in Protein-Nucleic Acid Interaction, Topics in Molecular and Structural Biology, Saenger and Heinemann (eds.), Macmillan, London, Vol. 10, pp. 143–162 (1989)).

Tetracycline analogs can be any one of a number of compounds that are closely related to tetracycline and which bind to the tet repressor with a Ka of at least about $10^6$ M$^{-1}$ (e.g., doxycycline). Preferably, the tetracycline analogs binds with an affinity of about 109 M-1 or greater, e.g., binds with an affinity of about 1011 M-1. Examples of such tetracycline analogs include, but re not limited to those disclosed by Hlavka and Boother, "The Tetracyclines," IN: Handbook of Experimental Pharmacology 78, R. K. Blackwood et al. (eds.), Springer-Verlag, Berlin-New York, 1985; Mitschef, "The Chemistry of the Tetracycline Antibiotics," Medicinal Research 9, Dekker, New York, 1978; Noyee Development Corporation, "Tetracycline Manufacturing Processes," Chemical Process Reviews, Park Ridge, N.J., 2 volumes, 1969; Evans, "The Technology of the Tetracyclines," Biochemical Reference Series 1, Quadrangle Press, New York, 1968; and Dowling, "Tetracycline," Antibiotics Monographs no. 3, Medical Encyclopedia, New York, 1955; each of which are incorporated herein by reference with respect to tetracycline analogs.

Inducible Promoters

In general, the inducible promoter used in conjunction with the transactivator in the inducible expression system of the invention is any promoter from which transcription can be regulated by the transactivator level.

For example, where the transactivator is a tetR polypeptide, the inducible promoter is preferably a minimal promoter containing at least one tetO sequence, preferably at least 2 or more tandemly repeated tetO sequences, even more preferably at least 5 or more tandemly repeated tetO sequences, more preferably at least 7 tandemly repeated tetO sequences or more. The minimal promoter portion of the inducible promoter can be derived from any desired promoter, and is selected according to tet cell line in which the inducible expression system is to be used. Where the cell is a mammalian cell, a preferred minimal promoter is derived from CMV, preferably from the CMV immediate early gene 1A. In addition other inducible promoters could be employed, such as the ecdysone-inducible promoters (Invitrogen Inc., San Diego, Calif.) or the lacZ inducible promoters.

Preferably, the inducible promoter is a minimal promoter operatively linked to at least one tet operator (tetO) sequence. The tetO sequence can be obtained, for example, according to Hillen & Wissmann 1989, supra, each of which are herein incorporated by reference with respect to the description and sequence of tetO. Other tetO sequences that can be used in the practice of the invention can be obtained from the following references: Waters et al., 1983, supra; Postle et al., 1984, supra; Unger et al., 1984, supra; Unger et al., 1984, supra; Tovar et al., 1988, supra; for comparison and overview see Hillen and Wissmann 1989, supra, the disclosures of which are filly herein incorporated by reference. One, two, three, four, five, six, seven, eight, nine or ten or more copies of the tet operator sequence can be used. Because multiple copies of the tet operator sequence provide a synergistic effect on the ability to control expression from these tetO-containing promoter, promoters having a greater number of copies of tetO allow an enhanced range of transactivator regulation of transcription from the promoter. Regulation of tetracycline-regulatable promoters containing tetO sequences is discussed in U.S. Pat. No. 5,464,758, and in Gossen and Brujand, 1992 Proc. Natl. Acad. Sci. USA 89:5547–5551, each of which are herein incorporated by reference.

Constructs

The basic components of the inducible expression system, e.g., the nucleotide sequence encoding the transactivator and the inducible promoter operably linked to a nucleotide sequence of interest, can be contained within a single "construct" or vector or within separate constructs. The construct can be derived from any of a variety of constructs know in the art and/or commercially available, and can be capable of replication in prokaryotic cells, eukaryotic cells, or, preferably, both prokaryotic and eukaryotic cells.

In addition to the components described above, the construct can additionally contain nucleotide sequence encoding gene(s) that can serve as selectable markers, e.g., antibiotic resistance genes (e.g, ampicillin, hygromycin, G418), β-galactosidase, or other gene products that can be used for selection of cells containing the construct. The construct can additionally contain other expression-facilitating sequences, such as enhancers, introns, or other sequences that facilitate expression of the transactivator and/or, where appropriate, expression of the nucleotide sequence of interest operably linked to the inducible promoter. In addition, indicators, such as green fluorescent protein (GFP) are useful in the constructs of the invention.

Introduction of the Inducible Expression System into Host Cells

In another embodiment, the invention provides a method for producing a packaging cell line. The method includes transfecting a suitable cell, as described herein, with a first polynucleotide having an HIV genome operably linked to a first inducible promoter wherein the HIV genome is defective for cis-acting elements, for self-replication and for expression of functional Env protein; a second polynucleotide encoding a functional heterologous Env protein operably linked to a second inducible promoter; and a third polynucleotide encoding a regulatable transcriptional activator controlling transcription from the first and second inducible promoters; and culturing the transfected cells of under conditions which allow screening for cells containing proteins encoded by the polynucleotides.

Any eukaryotic cell line that can be stably transformed with the inducible expression system of the invention and the nucleotide sequence(s) expressing the essential retroviral components (e.g., Gag and Pol), and express sufficient levels of the essential retroviral components and inducibly express the desired envelope protein for the production of recombinant retroviral vectors according to the invention can be used to generate a packaging cell line according to the invention. Suitable host cells include cells of both mammalian (e.g., human, simian, canine, feline, equine, and rodent) and non-mammalian origin (e.g, insect, reptile, fish and avian). The packaging cells can be either an in vitro cell culture or present in an organism in vivo.

Preferably, the packaging cells are present in an in vitro culture and can be cultured in a manner that allows for mass production of the recombinant retroviral vectors so as to provide suitable titers useful for production of the retroviral vector preparations for various applications (e.g., for clinical application in gene therapy). Where large-scale production of virus is desirable, the host cell from which the packaging cell is derived is preferably easy to culture, stable in long term culture (e.g., healthy cells can be maintained at relatively high cell densities for several days to several weeks or months, and do not undergo any significant genetic changes that might affect reliable production of consistent retroviral vector titers and/or the homogeneity of the genetic composition of the retroviral particles), and allows easy isolation of virus from the cell culture (e.g., by collection and concentration of cell culture supernatant to provide a crude retroviral particle preparation of an acceptable viral titer).

As exemplified herein, the inducible expression system is introduced into a host cell as separate recombinant polynucleotide sequences (e.g., one encoding the transactivator and one encoding the gene product of interest under control of the inducible promoter). Introduction of the nucleotide sequence encoding the inducible expression system into host cells can be accomplished either in vitro or in vivo according to methods well known in the art (see, e.g., Sambrook et al., 1987 Molecular Cloning: A Laboratory Manual, Cold Spring Harbor Press, Cold Spring Harbor, N.Y.) In a preferred embodiment, the inducible expression system is introduced into the host cell by infection with a retroviral vector, the polynucleotide sequence encoding the transactivator and/or the inducible promoter operably linked to the polynucleotide sequence encoding the desired envelope protein, and the polynucleotide sequence encoding the inducible expression system is stably integrated into the host cell genome.

Packaging Cell Lines Using the Inducible Expression System

The inducible expression system of the invention is used to generate packaging cells useful in the production of recombinant pseudotyped retroviral vectors, which are suitable for use in the introduction of a DNA sequence of interest into a target cell. Pseudotyped retroviral particles are retroviral particles having an envelope protein that is derived from a virus other than the virus from which the viral RNA genome is derived. The envelope protein can be from a retrovirus of a species different from the retrovirus from which the RNA genome is derived or from a non-retroviral virus (e.g., vesicular stomatitis virus (VSV)). Normally, the pseudotyped lentiviral or retroviral vectors are defective, i.e., the retroviral vector is derived from a naturally-occurring virus that has been genetically altered to render the virus replication-defective. Once the virus delivers its genetic material into a target cell, the virus introduces the recombinant nucleotide sequence into cell, preferably as a stably chromosomally integrated sequence, but does not generate additional infectious virus upon expression of the introduced retroviral sequence. Alternatively, the retroviral vector containing the nucleotide sequence of interest is attenuated, i.e. does not cause significant pathology or morbidity in the infected host (i.e., the virus is nonpathogenic or causes only minor disease symptoms).

Thus, in another embodiment of the invention, a method for producing a recombinant retrovirus which includes transfecting a packaging cell line as described herein with a lentiviral vector (e.g., a retroviral vector) including a polynucleotide encoding a packaging signal, an exogenous non-HIV polynucleotide, an RNA-export signal and lentiviral LTR sequences. A preferred RNA-export signal is a Rev response element.

The exogenous non-HIV polynucleotide encodes a polypeptide which includes a growth factor, a cytokine, a hormone, a neurotrophic factor and an immunoregulatory agent. Such polypeptides are useful for gene therapy using a recombinant lentivirus produced by the method of the invention and include but are not limited to interleukins 1 through 15, interferons, and in particular gamma interferon (γ-IFN), tumor necrosis factor (TNF), granulocyte-macrophage-colony stimulating factor (GM-CSF), and nerve growth factor (NGF).

Pseudotyped lentiviral or retroviral particles can be produced by introducing a defective, recombinant lentiviral, or more specifically, retroviral genome into a packaging cell (e.g., by infection with a defective retroviral particle, or by other means for introducing DNA into a target cell (e.g., conventional transformation techniques)). The defective retroviral genome minimally contains the long terminal repeats, the exogenous nucleotide sequence of interest to be transferred, and a packaging sequence (φ). In general, the packaging cell provides the missing retroviral components essential for retroviral replication, integration, and encapsidation, and also expresses a nucleotide sequence encoding the desired envelope protein. However, the packaging cell does not have all of the components essential for the production of retroviral particles. The nucleotide sequence(s) encoding the missing viral component(s) in the packaging cell can be either stably integrated into the packaging cell genome, and/or can be provided by a co-infecting helper virus.

The nucleotide sequences encoding the retroviral components and the lentiviral or retroviral RNA genome can be derived from any desired lenti- or retrovirus (e.g., murine, simian, avian, or human retroviruses). Most defective retroviruses developed for gene therapy applications are murine retroviruses (e.g., murine leukemia virus (MuLV), Moloney murine leukemia virus (MoMLV)), (see, e.g., Miller et al. 1992 Nature 357:455–460; and Mulligan 1993 Science 260:926–932). In general, the retroviral components can be derived from any retrovirus that can form pseudotyped retroviral particles with the desired envelope protein, e.g., VSV G. Where VSV G is the desired envelope protein, the retroviral components can be derived from MuLV, MoMLV, avian leukosis virus (ALV), human immunodeficiency virus (HIV), or any other retrovirus that can form pseudotyped virus with VSV G as the only envelope protein or with VSV G and a relatively small amount of retroviral envelope protein.

In one example of a pseudotyped retrovirus produced according to the present invention, the free virion form of pseudotyped defective murine retrovirus contains the structural and enzymatic proteins of the retrovirus (including reverse transcriptase), two RNA copies of the retroviral genome, and portions of the cell's plasma membrane in which is embedded the desired viral envelope glycoprotein (e.g., VSV G). The genome is organized into four main regions: the long terminal repeat (LTR), the gag gene, the pol gene, and the env gene. The three genes gag, pol, and env, which are located between the terminal LTRs, encode internal viral structural proteins and reverse transcriptase, respectively, and the env gene encodes the envelope glycoprotein that confers infectivity and host range specificity to the virus. Preferably, the retroviral genome is defective in one or all three of these genes. In addition, the retroviral genome can contain a nucleotide sequence of interest to be ultimately transferred to a target cell. When the defective, recombinant retroviral genome is integrated into the host cell in its proviral form, the LTR is positioned at both ends of the proviral genome, and is a composite of the 5' and 3' ends of the RNA genome. The LTR contains cis-acting elements necessary for the initiation and termination of transcription.

An exemplary packaging cell of the invention contains genes encoding Gag and Pol, as well as the desired envelope protein, but does not contain the packaging signal "φ" or the LTRs described above. Thus, a packaging cell can only form empty virion particles; once a retroviral RNA genome (which contains the nucleotide sequence of interest) is introduced into the packaging cell, the packaging cell can produce pseudotyped, defective retroviral particles. Packaging cells thus provide the missing retroviral components (i.e., the components for which the retroviral genome is defective) essential for viral replication in trans. Methods for production of replication-deficient retroviral genomes containing a nucleotide sequence of interest, as well as methods for generating a cell line expressing the gag and pol genes, are well known in the art and are described in, for example, U.S. Pat. No. 4,861,719; PCT published application no. WO 92/05266, published Apr. 2, 1992; and PCT published application no. WO 92/14829, published Sep. 2, 1992, each of which are incorporated herein by reference with respect to production of replication-deficient retroviral genomes and packaging cell lines expressing retroviral gag and pol genes. Retroviral packaging cell lines can be derived from any mammalian or non-mammalian cell that can express the retroviral Gag and Pol proteins, and can express the desired envelope protein (e.g., can tolerate expression of VSV G for several hours to several days, preferably for at least one week to two weeks or more). Preferably, the cell line from which the packaging cell line is derived is a cell selected from a liver, stroma, myogenic, fibroblast, and embryonic stem cell. Exemplary cells used by those of skill in the art for development of packaging cell lines include: 293 (ATCC CCL X) HeLa (ATCC CCL 2), D17 (ATCC CCL 183), MDCK (ATCC CCL 34), BHK (ATCC CCL-10), or Cf2Th (ATCC CRL 1430) cell, most preferably a 293 cell, each of which are publicly available from the ATCC. The exemplary cell line of the invention is referred to as SODK1293 or SODK1.

Pseudotyped retroviral particles are produced according to the invention by introducing a defective, recombinant retroviral genome containing a nucleotide sequence of interest into a packaging cell line that contains nucleotide sequences encoding for 1) functional retroviral proteins for which the introduced RNA genome is defective (e.g., gag and pol), and 2) an inducible expression system of the invention that facilitates expression of a desired envelope protein. The defective, recombinant RNA genome can be introduced into the packaging cell line by any means, including infection with a defective viral particle or other conventional means of transformation. Preferably, the packaging cell expresses a retroviral Gag protein, a retroviral Pol protein, and a desired envelope protein that is inducibly expressed using the system of the invention. The inducible expression system can be introduced as a single construct or as multiple constructs as described above and in the Examples.

The inducible promoter is preferably a minimal promoter derived from a CMV early gene promoter which is operably linked to at least one tetO sequence, preferably at least 2 or more tandemly repeated tetO sequences.

The nucleotide sequence encoding the desired envelope protein for production of retroviral particles is preferably a nucleotide sequence encoding a viral envelope protein derived from a virus other than the virus from which the Gag, Pol, and/or RNA genome are derived. Preferably, the viral envelope protein is derived from a retrovirus (e.g., a xenotropic retrovirus, a polytropic virus, an ecotropic or an amphotropic virus, preferably an amphotropic virus) or a non-retroviral virus, e.g., a rhabdovirus, Sindai virus, influenza virus, sindis virus, or herpes virus. In a preferred embodiment, the nucleotide sequence encoding the desired envelope protein encodes a rhabdovirus envelope G protein, such as the envelope protein of vesicular stomatitis virus (VSV), or a functional derivative thereof.

The nucleotide sequence encoding VSV G is described in Rose et al. 1982 Cell 30:753–762, herein incorporated by reference with respect to disclosure of the VSV G nucleotide and amino acid sequences. Where the desired envelope protein is VSV G, VSV G can be present as the only envelope protein in the pseudotyped retroviral virion, or can be present in combination with other envelope proteins (e.g., the retroviral envelope protein normally associated with the retrovirus from which the retroviral components of other pseudotyped virion are derived). Preferably, VSV G is present in the viral envelope such that VSV G represents about 50% of the envelope proteins present in the viral envelope, more preferably about 75%, even more preferably about 90% to about 95%, still more preferably greater than 95%, most preferably about 100% or such that VSV G is substantially the only envelope protein in the viral envelope. VSV G can be a native (i.e., naturally-occurring) VSV G, or a functional derivative thereof.

Functional derivatives of VSV G include, but are not limited to, VSV G-derived polypeptides having amino acid substitutions, deletions, additions, and/or chemical modifications relative to native VSV G. Functional VSV G derivatives thus include, but are not limited to, VSV G-derived polypeptides having a function different from or in addition to that normally associated with native VSV G. For example, VSV G can be fused to a polypeptide derived from an antibody having binding affinity for a tissue-specific or cell-specific antigen. Pseudotyped viral particles having such a VSV G-single chain antibody fusion protein present in the viral envelope can preferentially infect cells expressing on their surface the antigen to which the antibody chain binds. Other VSV G functional derivatives can likewise alter the host cell range of the pseudotyped viral particle and/or provide other desired characteristics. In general, any VSV G functional derivative that can form pseudotyped retroviral virions according to the invention can be used.

When the envelope-expressing packaging cell is exposed to tetracycline (or an analog thereof), substantially no or very little VSV G is expressed from the inducible promoter. In the absence of tetracycline, expression of the envelope protein is increased from about 10-fold to about 50-fold, preferably from about 40-fold to 90-fold, more preferably from about 40-fold to 100-fold, and may be 200-fold or more relative to transcription in the presence of tetracycline. In addition, expression of the transactivator can be regulated by operably linking the nucleotide sequence encoding the transactivator to a regulatable promoter. Thus the packaging cell of the invention can provide two or more levels of regulation of expression of the desired envelope protein: 1) negative regulation of expression of the envelope protein by the addition of tetracycline; 2) positive regulation by removing tetracycline; and, optionally, 3) regulated expression of the nucleotide sequence encoding the transactivator.

The packaging cell line of the invention capable of inducible expression of a desired envelope protein can be used to produce pseudotyped retroviral vectors at pre-centrifugation viral titers of at least more than $10^4$/ml, preferably more than $10^5$/ml, even more preferably more than $10^6$/ml. Preferred packaging cell lines of the invention produce viral titers of at least $10^5$ infectious particles per ml, preferably at least $5 \times 10^5$ per ml, more preferably at least $10^6$ per ml, and can produce viral titers of $1 \times 10^7$ per ml or more. Preferred packaging cell lines can produce viral titers on the order of at least about 1 viral particle/cell, preferably about 10 viral particles per cell, more preferably about 100 viral particles per cell or more. Preferred packaging cell lines can also be characterized by a viral titer produced over a unit of time. For example, preferred packaging cells of the invention produce about $10^4$ infectious particles per ml per hour, preferably about $10^5$ particles per ml per hour, and can produce up to about $10^6$ particles per ml per hr or more.

The packaging cells can be maintained under conditions that allow for production of infectious pseudotyped virions (e.g, in the absence of tetracycline) for at least 4 days, preferably at least 7 days, even more preferably at least 12 days, and can be maintained for 16 days or longer. For example, 293 cells can be maintained at least 7 days after induction with high virus productivity (e.g., from about $10^4$ to about $10^6$ cfu/ml or greater). Preferably, the packaging cells provide a higher titer in a shorter period of viral production time (i.e., as opposed to a lower viral titer over a longer period of viral production.

Preferably, the packing cells of the invention respond within a short time after induction, i.e., the packaging cells respond quickly to produce pseudotyped virus when tetracycline is removed from the media. Preferably, the packaging cells produce detectable viral titers within 48 hours after induction, more preferably within 12 hours to 24 hours after induction. Preferably, the packaging cells of the invention produce viral titers of at least $10^3$ cfu/ml, more preferably at least $10^4$ cfu/ml, still more preferably at least $10^5$ cfu/ml, most preferably $10^6$ cfu/ml or more within 5 days after induction, preferably within 4 days after induction, more preferably within 3 days after induction, still more preferably within 2 days after induction, and may produce such viral titers within 48 hours to 36 hours or less after induction.

In general, the pseudotyped virus packaging cell lines of the invention can produce $10^4$ to $10^6$ infectious viral particles per ml, provide virus production within a short time (e.g., within 24 hours to 48 hours) after removal of tetracycline and can produce infectious virus for about 5 days to about 16 days or more.

The packaging cells of the invention are preferably derived from cells that are easy to maintain in culture, can be grown to high densities, can be efficiently transfected using conventional techniques, and can tolerate levels of transactivation and desired envelope protein necessary to allow inducible expression of viral envelope and production of pseudotyped retroviral vectors. Repression of envelope protein production is preferably very tight (e.g., even a small amount of tetracycline, results in repression of viral envelope expression, and response to induction of expression is rapid (e.g., preferably within 12 hours to 36 hours after removal of tetracycline). For example, 293 cells grow like regular fibroblasts, are easy to culture, and exhibit a high DNA transfection efficiency (e.g., by the conventional calcium-phosphate co-precipitation method), making genetic manipulation of this cell line very easy.

Gene Transfer

In one embodiment, the packaging cells are present within a transgenic animal for in vivo production of pseudotyped retroviral particles that can be harvested from the animals (e.g., by collecting and isolating pseudotyped virions from the animal's blood or any other body fluid). The nucleotide sequence(s) encoding the retroviral Gag and Pol proteins and the nucleotide sequence(s) encoding the inducible expression system can be used to generate transgenic animals according to methods well known in the art as described above. The animals can then be infected with infectious, replication defective retroviral virions containing the nucleotide sequence of interest, which can then infect the "in vivo" packaging cells present in the transgenic animal to produce high titers of pseudotyped retroviral vector particles. Expression of the envelope protein encoded by the inducible expression system can be regulated by administration of tetracycline to the transgenic animal as described above.

In another embodiment, the present invention provides a method for introducing an exogenous non-HIV polynucleotide into the chromosome of a recipient cell. The method includes contacting a recipient cell with a recombinant lentivirus produced by the method of the invention; and integrating the exogenous non-HIV polynucleotide into the chromosome. The pseudotyped retroviral vector particles generated using the packaging cells of the invention can be used to facilitate delivery of a nucleotide sequence of interest to a host cell either in vitro or in vivo. For example, the pseudotyped retroviral vector particles can be used in gene therapy applications to deliver therapeutic gene product-encoding sequence to a subject, e.g., a mammalian subject, preferably a human subject. The pseudotyped retroviral vector particles can also be used to develop various disease or development animal or in vitro models. Recipient cells for delivery of lentiviral or retroviral vector particles of the invention include endothelial cells, myeloid cells, bone marrow cells, stem cells, lymphocytes, hepatocytes, fibroblasts, lung cells, muscle cells, embryonic cells, and neuronal cells. Methods for administration of retroviral particles to a subject to accomplish in vivo transformation are well known in the art (see, e.g., Mulligan 1993 Science 260:926; Anderson 1992 Science 256:808; Miller 1992 Nature 357:455; Crystal 1995 Science 270:404). Methods for transformation in vitro using retroviral particles are also well known in the art.

A variety of genes or DNA fragments can be incorporated into the retroviral vector particles of the invention for use in gene therapy. Protein of use in gene therapy include various hormones, growth factors, enzymes, lymphokines, cytokines, receptors and the like.

Among the genes that can be transferred in accordance with the invention are those encoding polypeptides that are absent, are produced in diminished quantities, or are produced in mutant form in individuals suffering from a genetic disease. Other genes of interest include those that encode proteins that have been engineered to circumvent a metabolic defect or proteins that, when expressed by a cell, can adapt the cell to grow under conditions where the unmodified cell would be unable to survive, or would become infected by a pathogen.

In addition to protein-encoding genes, the present invention can be used to introduce nucleic acid sequences encoding medically useful RNA molecules into cells. Examples of such RNA molecules include anti-sense molecules and catalytic molecules, such as ribozymes.

Retroviral vector particles of the invention can be used for ex vivo gene therapy in accordance with various techniques known in the art. In general terms, these techniques involve the removal of target cells of interest from a patient, incubation of the target cells with the retroviral vector particles, and reintroduction of the transduced target cells into the patient. Techniques for administration of retroviral vector particles produced by the packaging cells of the invention include those described in U.S. Pat. No. 5,580,766. This patent and its teachings are herein incorporated by reference in its entirety.

Methods of Detecting and Modulating HIV Integrase Activity

At present, HIV integrase is the only viral enzyme for which clinically useful inhibitors are not available. Thus, the development of an assay which utilizes preintegration complexes (PICs) represents an important tool for identifying integration inhibitors. Typically, screens are conducted using purified integrase protein alone, but such assays are only partially reflective of integration in vivo. The use of retroviral vectors obviates the biohazard associated with HIV-1 PICs and the vector cell line is a more robust and convenient source of viral particles. The present invention provides a method for screening PICs in a relatively high through-put fashion.

Accordingly, the invention provides a method of detecting a viral nucleic acid sequence integrated into a target nucleic acid sequence by reversibly immobilizing the target nucleic acid sequence to a solid support, contacting the target nucleic acid with a viral preintegration complex (PIC) containing the viral nucleic acid sequence, under such conditions and for sufficient time so as to allow the viral nucleic acid sequence to integrate into the target nucleic acid sequence and detecting the integrated viral nucleic acid sequence.

The invention further provides a method of detecting viral integrase activity contained in viral preintegration complex (PIC) by reversibly immobilizing a target nucleic acid sequence to a solid support; contacting the target nucleic acid with the viral preintegration complex (PIC) containing a viral nucleic acid sequence, under such conditions and for sufficient time so as to allow the viral nucleic acid sequence to integrate into the target nucleic acid sequence and detecting the integrated viral nucleic acid sequence. The presence of the viral nucleic acid sequence in the target nucleic acid sequence is indicative of integrase activity.

In one embodiment, the invention provides a method of identifying a compound that affects viral integrase activity contained in a preintegration complex (PIC). The method includes reversibly immobilizing a target nucleic acid sequence to a solid support; contacting the target nucleic acid with the viral preintegration complex (PIC) containing a viral nucleic acid sequence and a test compound suspected of affecting integrase activity, under such conditions and for sufficient time so as to allow the viral nucleic acid sequence to integrate into the target nucleic acid sequence; and detecting the integrated viral nucleic acid sequence. The amount of viral nucleic acid sequence integrated in the target nucleic acid sequence is indicative of the effect of the compound on integrase activity.

Thus, the invention provides a method for identifying a compound which modulates integrase activity. The method includes incubating components comprising the compound, integrase, a nucleic acid to be integrated and a target nucleic acid under conditions sufficient to allow the components to interact and determining the effect of the compound on the activity of the integrase before and after incubating in the presence of the compound. Preferably, the integrase is HIV integrase. HIV integrase can be isolated as a part of a preintegration complex (PIC). Compounds that modulate HIV integrase activity can include peptides, peptidomimetics, polypeptides, chemical compounds and biologic compounds. The term "modulate", as used herein, encompasses any means by which integrase activity can be affected, such as inhibition of activity or an increase in activity. The activity of the integrase can be assayed using methodology as described in Example 3 (e.g., based on PCR and agarose gel electrophoresis) or by other standard methods known in the art.

Incubating includes conditions which allow contact between the test compound, the integrase and the target nucleic acid. The test compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 3:1008–1012, 1985), allele-specific oligonucleotide (ASO) probe analysis (Conner, et al., Proc. Natl. Acad. Sci. USA, 80:278, 1983), oligonucleotide ligation assays (OLAs) (Landegren, et al., Science, 241:1077, 1988), and the like. Molecular techniques for DNA analysis have been reviewed (Landegren, et al., Science, 242:229–237, 1988).

The method of the invention includes combinatorial chemistry methods for identifying chemical compounds that bind to integrase or affect integrase expression or activity. By providing for the production of large amounts of HIV integrase, one can identify ligands or substrates that bind to, modulate, affect the expression of, or mimic the action of HIV integrase.

Areas of investigation are the development of therapeutic treatments. The screening assay described herein identifies compounds that provide modulation of HIV integrase function in targeted organisms. Of particular interest are screening assays for compounds that have a low toxicity for humans. A wide variety of assays may be used for this purpose, including labeled in vitro protein-protein binding assays, protein-DNA binding assays, electrophoretic mobility shift assays, immunoassays for protein binding, and the like. The purified protein may also be used for determination of three-dimensional crystal structure, which can be used for modeling intermolecular interactions and transcriptional regulation, for example.

The term "compound" as used herein describes any molecule, e.g. protein or pharmaceutical, with the capability of altering the physiological function or expression of HIV integrase. Generally, a plurality of assay mixtures are run in parallel with different compound concentrations to obtain a differential response to the various concentrations. Typically, one of these concentrations serves as a negative control, i.e. at zero concentration or below the level of detection.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors and anti-microbial agents may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

The present invention provides a method useful for detecting viral integration by attaching a target nucleic acid to a substrate associated with a solid support and contacting the target nucleic acid with PICs. It is envisioned that any substrate useful for conjugating a target nucleic acid to a solid support can be used in the present method. Such conjugation is preferably a chemical conjugation. Chemical conjugation useful for attaching a nucleic acid to a particular substrate can be accomplished by any method known to those of skill in the art. Such methods may include, for example, chemical conjugation of a nucleic acid to a substrate by a disulphide bridge. In the preceding example, the nucleic acid-substrate complex can be disrupted by the addition of a reducing agent such as, for example, beta mercaptoethanol. Another example of chemical conjugation can include a double-stranded target nucleic acid having a reactive 5' phosphate covalently bound to amine groups attached to a solid support. Subsequent treatment with NaOH disrupts the 5' phosphate-amine group conjugate thereby disociating the immobilized target nucleic acid-5' phosphate moiety from the amine group attached to the solid support.

Immobilization of substrates to the solid support material may occur via a variety of methods apparent to the skilled artisan. Solid supports useful for the present method are known to those of average skill in the art. The term "solid support", as used herein, is any structure which provides a supporting surface for the attachment of a substrate. Well known solid supports useful for the method of the invention include, but are not restricted to, glass beads, silica aerogels, agarose, Sepharose, Sephadex, nitrocellulose, polyethylene, dextran, nylon, natural and modified cellulose, polyacrylamide, polystyrene, polypropylene, and microporous polyvinylidene difluoride membrane. It is understood that any material which allows for the attachment and support of a target nucleic acid is included in the present invention. In Example 3 provided herein, a 96-multiwell plate was utilized as the solid support.

The following examples are intended to illustrate but not limit the invention. While they are typical of those that might be used, other procedures known to those skilled in the art may alternatively be used.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1

Materials and Methods

Plasmid Construction pSKVG was constructed by cloning the EcoRI VSV-G (Indiana serotype) from pMDG( Naldini et al., (1996) Science 272, 263–267) into the EcoRI site of Bluescript SK+ (Stratagene, La Jolla, Calif.). The GFP coding fragment was excised from pEGFP-N1 (Clontech) by SacI/NotI digestion and ligated to SacI/NotI fragment of Bluescript SK+ to create pSKGFP. A PstI fragment containing the GFP coding region from pSKGFP and NheI/EcoRV fragment containing the VSV-G coding region from pSKVG were ligated to PstI and XbaI/PvuII site in pBI (Clontech 6152-1) respectively, to create pBIGFVG.

BamHI/BglII fragment containing a minimal CMV immediate-early gene promoter linked to seven tandem copies of the tetR-binding site replaced the CMV promoter (BglII/BamHI fragment), in pcDNAneo to create phCMVn.

pPTK was constructed by ligation of BglI/SacII fragment encoding all the HIV-1 proteins from pDR8.2 (Naldini et al., supra) to BglI(partial)/SacII fragment from phCMVn. The XhoI fragment containing the neomycin resistance gene was deleted from ptTet-Off (Clontech K1620-A) to create ptTADn from which the a fusion protein containing the carboxy terminus of the tetracycline repressor and the herpes simplex virus VP16 transactivation domain is expressed under the control of the CMV promoter.

Generation of Lentiviral Vector Packaging Cell Line

All the cell lines in this study were maintained in Dulbeco's modified Eagle's containing tetracycline-free 10% fetal calf serum (Clontech 8630-1). To generate the stable cell line SODk0 that expresses the fusion protein tetracycline repressor /VP16 transactivation domain, human 293 embryonic kidney cells were cotransfected with 20 mg of ptTADn and 1 mg of pSRaBSR that expresses the blastocydine resistance gene, by a calcium phosphate precipitation method (Naldini et al., supra). Individual cell colonies were selected under 20 mg/ml of blsatocydine. The colonies were screened for tTA expression by transient transfection with 20 mg of pBIGFVG. Isolation of the 4 highest producer colonies was based on the number of fused cells and the level of GFP expression as determined by fluorescence microscopy. In order to determine which of the 4 colonies is most suitable for vector production the colonies were transfected with 5 mg of pBIGFVG, 10 mg pPTK, and 15 mg of HrcmvGFP (Miyoshi, et al. (1997) Proc. Natl. Acad. Sci. USA 94, 10319–10323.) 48 hours post transfection condition media was collected and viral titers on 293 cells were determined by serial dilution. The colony which was found to be the highest producer in 2 experiments (titer on 293>$2\times10^6$ I.U/ml) was chosen for generating the stable lentiviral vector packaging cell line.

The lentiviral vector stable packaging cell line SODk1 was generated by transfection of SODk0 cells with 10 mg of pPTK, and 10 mg of pBIGFVG. The transfected cells were selected for neomycin resistance (400 mg/ml) in the presence of 0.7 mg/ml doxycycline. Individual colonies were screened for HIV-1 p24 and GFP production and cell fusion in the presence or absence of doxycycline as follows. Cells from confluent 10 cm plate were split by ratio of 1/4 into PolyLysine precoated plates. Induced cells were cultured in the absence of doxycycline. Cell media was changed daily. Control cells were cultured in the presence of 0.7 mg/ml doxycycline. On day 4 post induction the levels of HIV-1 p24 in conditioned media was assayed by ELISA (DuPont). Cell fusion as a marker for VSV-G production, and GFP production was determined by fluorescence microscopy. The colony which was found to be negative for p24, and GFP, production in the presence of doxycycline and yet showed the highest levels of p24 production (>800 nng/ml) with more than 90% green cells upon induction was chosen as the packaging cell line for the lentiviral vector.

The lentiviral vector producer cell line SODk1CGFI was generated by transducing SODk1 cells with HRcmvGFP lentiviral vector at M.O.I of 2.

Vector Production from SODk1CGFI Cell Line

To test vector production capability, SODk1CGFI cells were split from confluent 10 cm plate into precoated Polylysine plate by ratio of 1/4 in the absence of doxycycline. 24 hours after split, the cells were washed twice with PBS and refed with doxycycline free media that contained 5 mM sodium butyrate. Doxycycline free media that contained 5 mM sodium butyrate was replenished daily. Induced SODk1CGFI conditioned media was filtered through a 0.45-mm-pore size filter and assayed daily for vector titers and p24 concentration in by serial dilutions on 293 cells and by p24 ELISA respectively.

In order to further concentrate the vector, conditioned media was collected 3 days after addition of sodium butyrate filtered as described before, and ultracentrifuged at 50,000×g for 2 hours. The pellet was resuspended and incubated for 2 hours at 37° C. in Tris-buffered saline (TBS) containing 10 mM MgCl2, four dNTPs (0.1 mM each), 3 mM spermine, and 0.3 mM spermidine. After a second ultracentrifugation at 50,000×g for 2 hours the was resuspended in TBS with 2 mg/ml Polybrene. The concentrated vector was assayed for p24 concentration, and titered on 293 cells as described before.

Western analysis was performed to test inducibility of VSV-G protein and HIV-1 Vpr production in SODk1CGFI cells. Induced (3 days after adding sodium butyrate) and non induced cells (cultured in the presence of doxycyline) were lysed and proteins denatured by boiling for 10' in a buffer containing 68 mM tris (pH6.8), 50 mM NaCl, 0.5 mM EDTA, 0.5 aprotinin, 50 mg/ml PMSF, 1.5%SDS, 5% glycerol, 5%b-mercaptoethanol. 20 mg of the denatured protein, were separated on 12.5% polyacrylamide gel containing SDS and blotted onto Immobilon-P membrane (Millipore), After blocking with 5% nonfat milk in PBS, 0.2% Tween20, for 15' the membranes were incubated with mouse monoclonal anti VSV-G (Sigma V-5507) or with rabbit HIV-1 Vpr (National Institute of Allergy and Infectious Diseases AIDS Research and Reference Reagent Program. reagent 3252) and then with goat anti-mouse Ig HRP (pierce), or donkey anti-rabbit horseradish peroxidase (Amersham) respectively. The protein bands were detected with an ECL kit (Amersham).

Transduction of Non-dividing Cells in Vitro

Serial dilution of induced SODkCGFVGI conditioned media were used to transduce HeLa cells arrested by culturing in the presence 15 mg/ml aphidicolin for 12 hours, HeLa cells cultured in the absence of aphidicolin, human embryo fibroblasts arrested by culturing for 48 hours in 0.1% fetal calf serum, and human embryo fibroblasts cultured in 10% fetal calf serum. Titers were scored 48 hours post transduction by number of GFP positive foci divided by the dilution factor.

Transduction of Terminally Differentiated Non Dividing Cells In Vivo

Adult female Fischer 344 rats were anesthetized as described (Naldini et al., supra) and 3 ml of concentrated vector ($1\times10^9$ I.U/ml) were injected into the left striatum (anterior posterior, +0.2; medial lateral, −3.5; dorsal ventral, −4.5) with a 5-ml Hamilton syringe. After 4 weeks the animals were sacrificed and perfused with 75 ml saline followed with 200 ml 4%paraformaldehyde, and 0.2% glutaraldehyde. The fixed brains were saturated in 30% sucrose, frozen and sectioned into 50-mm slices.

Primary antibodies were pooled in TBS with 10% donkey serum and 0.3% Triton X-100 and incubated for 48 hours at 4° C.

Example 2

Induction of SODk1 cells by doxycycline withdrawal in the presence of 5 mM sodium butyrate resulted in the production of HIV-1 proteins as determined by p24 ELISA. HIV-1 p24 could be detected from day 1 post induction to day 6 post induction after which significant cell death could be observed. Maximal levels of p24 were >800 nng/ml was detected at days 2 and 3 post induction. No p24 could be detected in non induced cells.

GFP production could be detected from day 2 post induction. Cell fusion as indicator for VSV-G production could be observed from day 3 post induction. Neither cell fusion nor GFP production could be detected by fluorescence microscopy in non-induced cells.

SODk1CGFI Cells

Induction of SODk1CGFI cells as described before resulted in the production of HIV-1 proteins as determined by p24 ELISA. HIV-1 p24 could be determined from days 1 to day 6 post induction. Maximal p24 levels (>1000 nng/ml) could be detected on day 2–3 post induction. Production of HIV-1 Vpr in induced cells was determined by western analysis.

VSV-G protein production in induced cells was determined by western analysis. Vector production by induced cells could be detected from day 1 to day 6 post induction. Maximal titer of $1.5 \times 10^6$ I.U as determined by serial dilution on 293 cells could be obtained on days 2–3 post infection. The vector could be concentrated by ultra centrifugation to $1 \times 10^9$ I.U.

The vector was shown to be able to transduce non-dividing cells in vitro and in vivo.

Vector titers on cultured arrested cells was not different from the titers on dividing cells. Injection of the vector into adult rat brain resulted in the transduction of terminally differentiated non-dividing neurons (for methods, see Cohen et al., 1996, Science 272:195, incorporated by reference in its entirety).

Production of HIV-1 p24 and Vpr proteins could not be detected in non-induced cells by ELISA or western analysis respectively.

Production of VSV-G protein could not be detected by western analysis in non-induced cells. Vector production could not be detected in non-induced cells.

Example 3

The invention further involves using an HIV-based vector produced by a cell line as described in the preceding Examples, to establish assays for retroviral integration in vitro. Supernatants containing HIV-based vector particles were derived from packaging cell lines as described herein. Exemplary packaging cell lines are derived from 293 HeLa, Cf2Th, D17, MDCK, or BHK cells, most preferably from 293 cells. The viral particles from these cell lines were concentrated and used to infect 293T target cells. The 293T cells were subsequently lysed and viral replication intermediates recovered. (See for example, (Farnet and Haseltine, PNAS 87:4164, 1990; Ellison et al., J. Virol., 64:2711, 1990, incorporated by reference). These intermediates, designated "preintegration complexes" (PICs) contain viral cDNA bound to viral and cellular proteins. One such viral protein, integrase, directs the covalent connection of viral cDNA to target DNA. Accordingly, the present method utilizes PICs to effect in vitro covalent integration of viral cDNA into an added target nucleic acid. Such methods are useful in the pharmaceutical industry for the rapid screening of integrase inhibitors and are of particular interest in HIV research.

Figure 1:
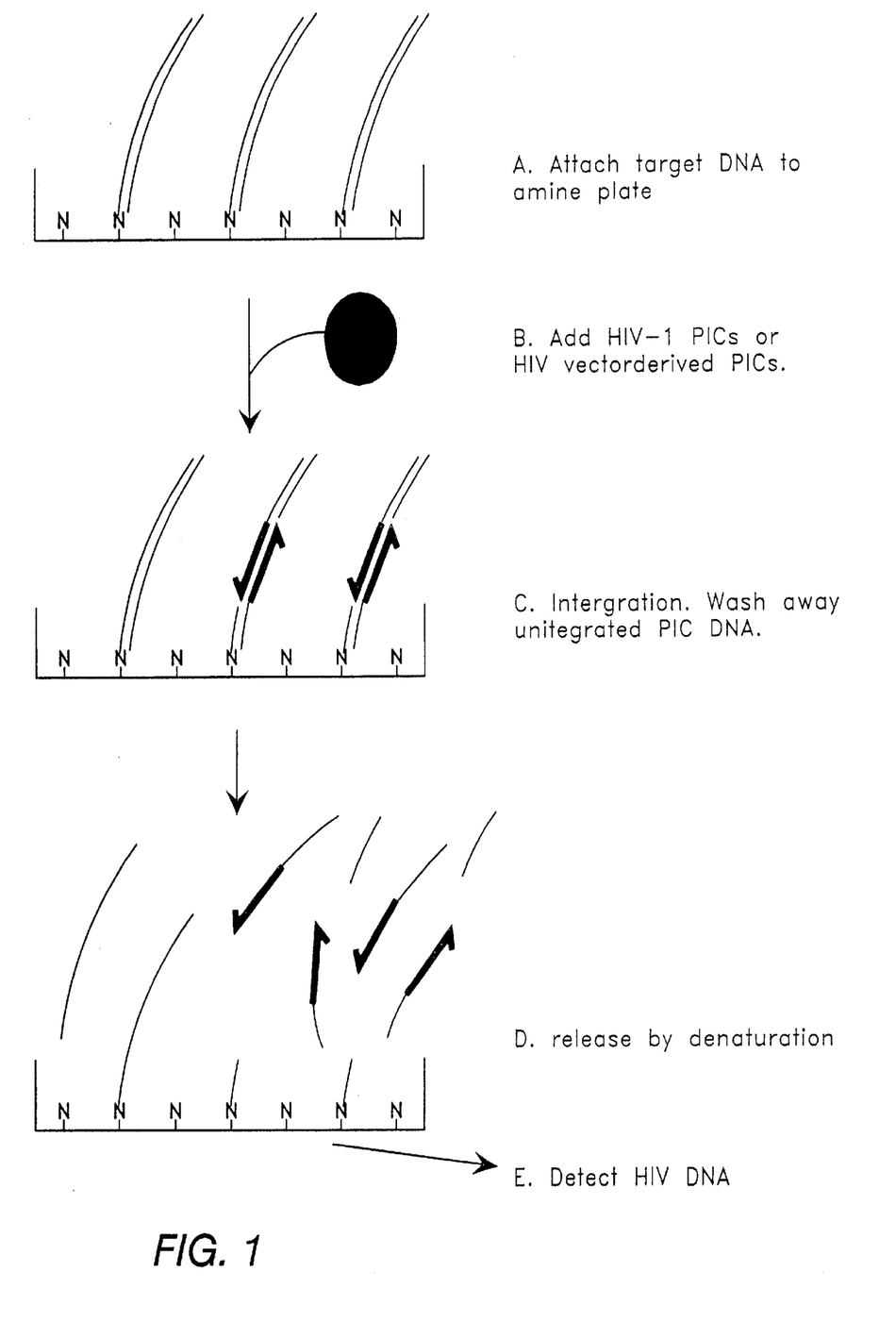
FIGS. 1A–1E shows a diagram of an assay useful for the detection of preintegration complex (PIC) integration activity. The figure shows a microtiter plate format.
Figure 2:
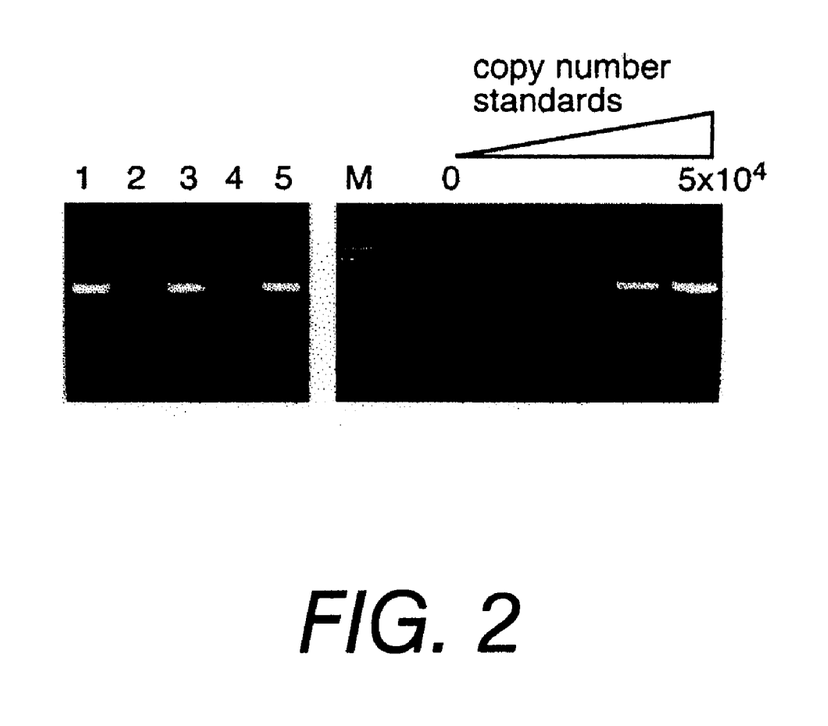
FIG. 2 shows an agarose gel of integration products released from amine plates subsequently amplified by PCR using primers complementary to HIV sequences.

The integration assay described here utilized 96-well microtiter plates. As shown in FIG. 1, linear, double-stranded target DNA having a reactive 5' phosphate (indicated by a dot) was covalently attached to an amine-coated microtiter well (FIG. 1A). The amine groups are represented by "N." HIV-based preintegration complexes (PICs) were added to the wells (FIG. 1B). The integration reaction yielded the covalent attachment of the viral cDNA (represented by the thick lines) 3' ends to target DNA. Unintegrated HIV cDNA molecules were washed away. The DNA strands were then released by NaOH denaturation (FIG. 1D). Integrated HIV nucleic acid contained in the released sequences were detected and quantified (FIG. 1E and FIG. 2). Integration products released from amine plates were amplified by PCR using primers complementary to HIV sequences and detected using agarose gel electrophoresis (FIG. 2). The results of five integration reactions are shown in FIG. 2: standard conditions, lane 1; with added 20 mM EDTA, lane 2; 15 mM MgCl2, lane 3; 0.1% SDS, lane 4; and 0.5% Tx-100, lane 5. Standard conditions were 150 mM KCl 20 mM Hepes pH 7.4, 5 mM MgCl2, 5% DMSO, and 0.2% BSA. A DNA marker, lane M, and copy number standards of HIV sequences are shown to the right.

Although the invention has been described with reference to the presently preferred embodiment, it should be understood that various modifications can be made without departing from the spirit of the invention. Accordingly, the invention is limited only by the following claims.

What is claimed is:

1. A method of detecting a viral nucleic acid sequence integrated into a target nucleic acid sequence comprising:
   a) immobilizing a target nucleic acid sequence to a solid support;
   b) contacting the target nucleic acid with a viral preintegration complex (PIC) containing a viral nucleic acid sequence, under conditions sufficient to allow the viral nucleic acid sequence to integrate into the target nucleic acid sequence;
   c) releasing the immobilized target nucleic acid sequence; and
   d) detecting the integrated viral nucleic acid sequence in the released target nucleic acid sequence.

2. The method of claim 1, wherein the viral preintegration complex (PIC) is isolated from HIV-infected cells.

3. The method of claim 1, wherein integration of the viral nucleic acid sequence in the target nucleic acid is detected using a polymerase chain reaction.

4. The method of claim 1, wherein integration of the viral nucleic acid sequence in the target nucleic acid is detected by nucleic acid probe hybridization under stringent conditions.

5. The method of claim 1, wherein the viral preintegration complex (PIC) is isolated from HIV vector infected cells.

6. The method of claim 1, further comprising quantifying the viral nucleic acid sequence in the released target nucleic acid sequence.

7. A method of identifying a compound that modulates viral integrase activity contained in a preintegration complex (PIC) comprising:

a) immobilizing a target nucleic acid sequence to a solid support;
b) contacting the target nucleic acid of a) with a viral preintegration complex (PIC) containing a viral nucleic acid sequence, under such conditions and for sufficient time so as to allow the viral nucleic acid sequence to integrate into the target nucleic acid sequence;
c) contacting the preintegration complex with a compound suspected of modulating integrase activity prior to, or simultaneously with, b);
d) releasing the immobilized target nucleic acid sequence; and
e) detecting the integrated viral nucleic acid sequence;
wherein the amount of viral nucleic acid sequence integrated in the released target nucleic acid sequence is indicative of the effect of the compound on integrase activity.

8. The method of claim 7, wherein the effect of the compound on integrase activity is inhibition.

9. The method of claim 7, wherein the viral integrase activity is HIV integrase.

10. The method of claim 7, wherein integration of the viral nucleic acid sequence in the target nucleic acid is detected using a polymerase chain reaction.

11. The method of claim 7, wherein integration of the viral nucleic acid sequence in the target nucleic acid is detected by nucleic acid probe hybridization under stringent conditions.

12. The method of claim 7, wherein the viral preintegration complex (PIC) is isolated from HIV vector infected cells.

13. The method of claim 7, further comprising quantifying the viral nucleic acid sequence in the released target nucleic acid sequence.

* * * * *